United States Patent [19]

Zook

[11] Patent Number: 5,415,866
[45] Date of Patent: * May 16, 1995

[54] TOPICAL DRUG DELIVERY SYSTEM

[76] Inventor: Gerald P. Zook, 802 W. 18th Pl., Eugene, Oreg. 97402

[ * ] Notice: The portion of the term of this patent subsequent to Dec. 1, 2009 has been disclaimed.

[21] Appl. No.: 89,192

[22] Filed: Jul. 12, 1993

[51] Int. Cl.⁶ .......................... A61K 9/70; A61F 13/02
[52] U.S. Cl. ......................... 424/448; 424/443; 424/447; 514/817; 602/48; 604/304; 604/307
[58] Field of Search .................. 424/443, 447, 448; 602/48; 604/303, 307; 514/817

[56] References Cited

U.S. PATENT DOCUMENTS

| | | | |
|---|---|---|---|
| 3,419,006 | 12/1968 | King | 128/268 |
| 3,814,095 | 6/1974 | Lubens | 128/260 |
| 4,158,359 | 6/1979 | Kurokawa | 128/630 |
| 4,379,454 | 4/1983 | Campbell et al. | 604/897 |
| 4,631,227 | 12/1986 | Nakamura | 428/283 |
| 4,788,971 | 12/1988 | Quisno | 128/743 |
| 4,842,931 | 6/1989 | Zook | 428/354 |
| 4,988,341 | 1/1991 | Columbus et al. | 604/306 |
| 4,991,574 | 2/1991 | Pocknell | 128/156 |
| 5,015,228 | 5/1991 | Columbus et al. | 604/51 |
| 5,098,421 | 3/1992 | Zook | 604/367 |
| 5,106,629 | 4/1992 | Cartmell et al. | 424/445 |
| 5,108,710 | 4/1992 | Little et al. | 422/104 |
| 5,167,649 | 12/1992 | Zook | 604/307 |
| 5,181,914 | 1/1993 | Zook | 604/307 |
| 5,331,012 | 7/1994 | Riddick et al. | 514/626 |
| 5,332,576 | 7/1994 | Mantelle | 424/443 |

*Primary Examiner*—Thurman K. Page
*Assistant Examiner*—James M. Spear
*Attorney, Agent, or Firm*—John F. Ingman

[57] ABSTRACT

A drug delivery system for the topical administration of medication which utilizes a viscoelastic gel pad having a liquid fraction, wherein the medication is incorporated within the liquid fraction, the viscoelastic gel pad being partially encapsulated between two layers of liquid fraction impermeable material which are joined together to form a seal about the periphery of the gel pad so as to control migration of the pad, and the medicating skin contact of the pad is limited to a drug delivery aperture formed in the skin-contacting layer of liquid fraction impermeable material. The aperture-containing layer, which contacts a wearer's skin, may be provided with a pressure sensitive adhesive. The invention is exemplified in a topical anesthetic delivery system wherein a viscoelastic gel pad, partially encapsulated by transparent alcohol and water impermeable layers, has an alcohol and water liquid fraction in which is dissolved lidocaine base. The alcohol and liquid fraction of the anesthetic viscoelastic gel pad may be from 20% to 90% alcohol, preferably 70% ethyl alcohol, wherein is dissolved 10% to 40%, by weight, of Lidocaine U.S.P./N.F. Such topical anesthetic drug delivery system can be preliminarily applied with accuracy to a target skin surface by a patient, leaving, upon subsequent removal, a target skin surface anesthetized and ready for immediate dermal surgery or other treatment.

5 Claims, 1 Drawing Sheet

TOPICAL DRUG DELIVERY SYSTEM

BACKGROUND OF THE INVENTION

1. Field of the Invention

This invention relates to the field of drug delivery systems for the topical administration of medication, and, more particularly, a topical drug delivery system utilizing a viscoelastic gel pad having a liquid fraction wherein the medication is incorporated within the liquid fraction, and still more particularly, a topical anesthetic delivery system using a viscoelastic gel pad having an alcohol and water liquid fraction wherein a topical anesthetic, such as lidocaine base, is dissolved in the alcohol and water liquid fraction.

2. Description of the Prior Art

The inventor previously has developed a Drug Delivery System For The Removal of Dermal Lesions, for which U.S. Pat. No. 5,167,649 was issued, which utilizes a viscoelastic rubber and oil gel which is partially encapsulated between two layers of oil and water impermeable material, where the skin contacting layer includes an aperture which is smaller than, and located within, the periphery of the pad. In conjunction with further development of pharmacological applications of the invention, it was discovered that the general inventive structure has additional medicating applications, and is particularly valuable in use as a topical anesthetic device.

Historically, dermal anesthesia for minor skin surgery has been achieved by the local infiltration of anesthetic solution via a needle and syringe. Although this technique is effective, it suffers from several drawbacks. Many patients, especially children, do not tolerate the pain of an injection well. Injection of a fluid into infected tissue can result in spread of the infecting organism(s) along the needle track. Additionally, injection of a bolus of local anesthetic into an allergic patient could result in a more severe reaction than a topically applied drug.

Generally speaking, local anesthetics do not penetrate into the skin in sufficient concentration to provide surgical anesthesia. In recent years, creams containing a Eutectic Mixture of Local Anesthetics (EMLA) such as lidocaine and prilocaine have been found useful as a topical anesthetic for superficial skin procedures. The EMLA cream is applied to a lesion and adjacent tissue and covered with an occlusive dressing for about 20 minutes to about 2 hours. More recently, a formulation of 30% lidocaine in an acid mantle cream has been found to be an effective and inexpensive topical anesthetic. While the EMLA and lidocaine creams are welcomed alternatives to anesthetic infiltration via injection, they have several drawbacks. For example, in the podiatric clinical setting, a cream applied to the foot and covered with an occlusive film would obviously smear when shoes were applied and the patient ambulated.

What is needed is a topical medicating device utilizing a viscoelastic gel pad having a liquid fraction wherein the medication is incorporated within the liquid fraction, where the viscoelastic gel pad is migration-controlled and the application of medication is limited to a specifically defined target skin surface. Such a topical drug delivery system is especially needed in the topical application of a local anesthetic.

SUMMARY OF THE INVENTION

Accordingly, it is an object of the present invention to provide a drug delivery system for the general topical administration of medicine which utilizes a viscoelastic gel pad having a liquid fraction, wherein the medication is incorporated within the liquid fraction, the viscoelastic gel pad being partially encapsulated between two layers of liquid fraction impermeable material so as to control migration of the pad, and the medicating skin contact of the pad is limited to a drug delivery aperture formed in the skin-contacting layer of liquid fraction impermeable material.

It is a further object of the present invention to provide a drug delivery system for the general topical administration of medications which is protective of the target skin surface.

It is a further object of the present invention to provide a topical drug delivery system which is transparent, allowing precise application of the aforementioned drug delivery aperture.

It is a further, and specific, object of the present invention to provide a topical anesthetic drug delivery system which can be preliminarily applied with accuracy to a target skin surface by a physician, health care worker or patient, leaving, upon subsequent removal, a target skin surface which is anesthized and ready for immediate dermal surgery or other treatment.

The present invention is exemplified in a topical anesthetic delivery system comprising a viscoelastic gel pad having an alcohol and water liquid fraction perfused with lidocaine base and partially encapsulated by transparent alcohol and water impermeable layers which allow direct contact by the anesthetic through a drug delivery aperture only upon the target skin surface being treated.

The preferred embodiment of a drug delivery system for topical anesthetics includes a pad of viscoelastic gel, having an alcohol and water liquid fraction, which is partially encapsulated between a first layer of alcohol and water impermeable material and a second layer of alcohol and water impermeable material. The second layer includes a drug delivery aperture which is smaller than, and located within, the periphery of the adjacent viscoelastic gel pad having an alcohol and water liquid fraction. The two layers of alcohol and water impermeable material are bonded together to form a seal about the periphery of the viscoelastic gel pad which controls gel pad migration. The aperture-containing layer, which in use contacts a wearer's skin, may be provided with a pressure sensitive adhesive.

The alcohol and water liquid fraction of the viscoelastic gel pad may range from about 20% to 90% alcohol, and preferably is approximately 70% ethyl alcohol, wherein is dissolved 10% to 40%, by weight, of Lidocaine U.S.P./N.F.

DESCRIPTION OF THE PREFERRED EMBODIMENT

Figure 1:
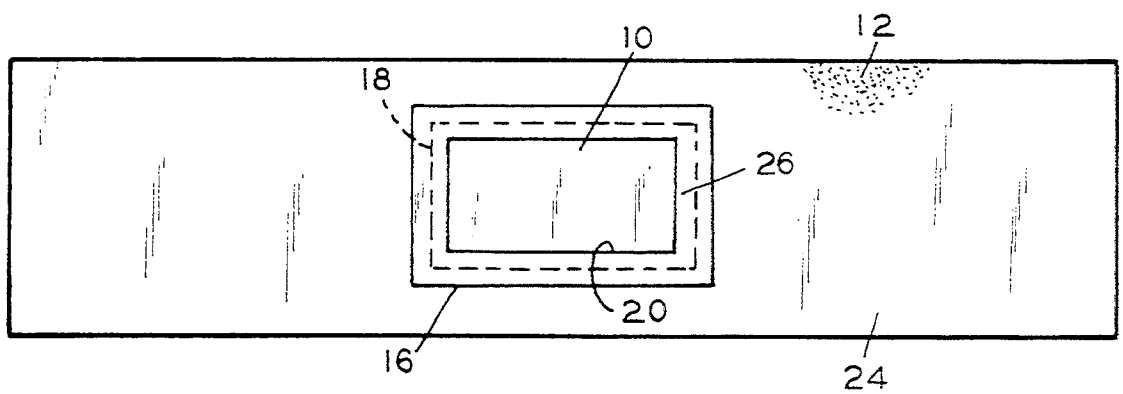
FIG. 1 is a plan view of a preferred embodiment of the drug delivery system for the topical administration of medications.
Figure 2:
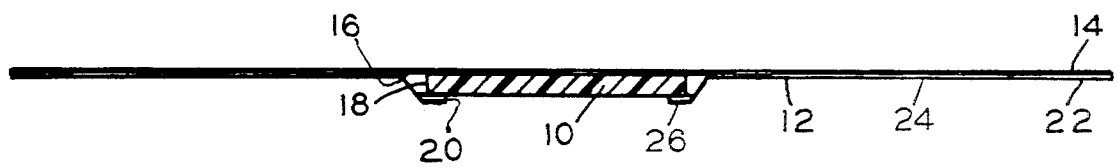
FIG. 2 is a cross-sectional side view of the drug delivery system of FIG. 1.
Figure 3:
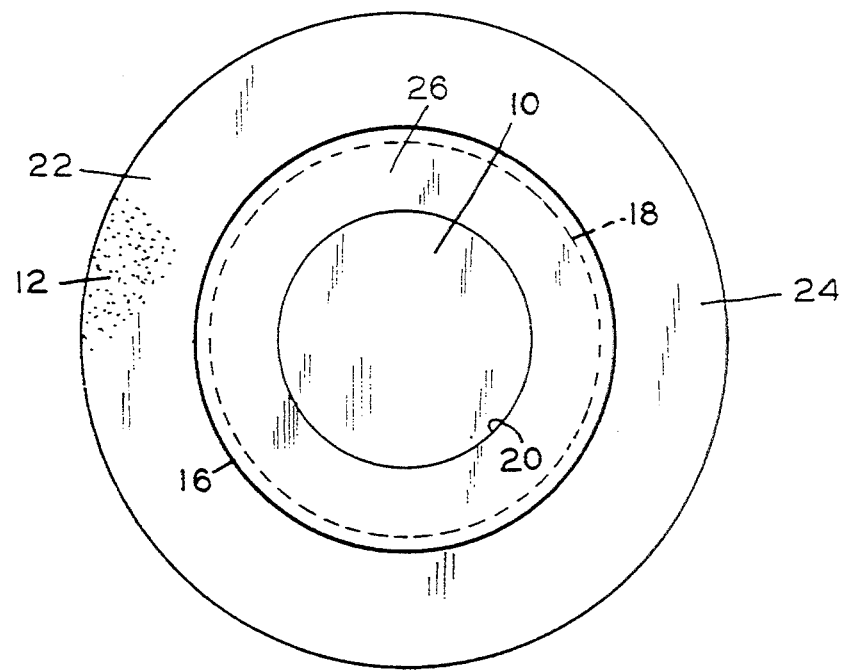
FIG. 3 is a plan view of an alternative shape of the drug delivery system for the topical administration of medications.

Turning now to the drawings, there is shown in FIGS. 1 and 2 a preferred embodiment of the topical drug delivery system, illustrated in a rectangular configuration in FIGS. 1 and 2, and in a circular configuration in FIG. 3.

The invention is exemplified in the following preferred embodiment for the application of a topical anesthetic, wherein a pad 10 of viscoelastic gel, having a alcohol and water liquid fraction in which the anesthetic in the form of lidocaine base has been dissolved, is partially encapsulated between a first layer 14 of alcohol and water impermeable material and a second layer 22 of alcohol and water impermeable material. The second layer 22 includes an aperture 20 for drug delivery which is smaller than, and located within, the periphery 18 of the adjacent viscoelastic gel pad 10. The aperture 20 is formed to correspond to the size of a target skin surface desired to be anesthized. The two layers of alcohol and water impermeable material, 14 and 22, are bonded together to form a seal 16 about the periphery 18 of the gel pad 10. The seal 16 about the periphery 18 of the gel pad 10 serves to restrict migration of the gel pad 10.

The margin 26 of layer 22 defines the aperture 20 which allows the gel pad 10 to come into direct contact with, and only with, the target skin surface to be anesthetized. The bond and seal 16 between the layers 14, 22 may be created by a thermal weld, or alternatively accomplished by adhesive or other means. Preferably both the viscoelastic gel pad 10 having an alcohol and water liquid fraction, and the layers 14 and 22 of alcohol and water impermeable material, are transparent, so as to readily permit precise application of the aperture 20 upon the target skin surface to be anesthized and to allow subsequent medical viewing thereof. The alcohol and water impermeable encapsulating layers 14 and 22 may be a transparent impermeable plastic, with layer 22, wherein the aperture 20 is formed, being provided on its surface 24 with a pressure sensitive adhesive 12.

The viscoelastic gel pad 10 having an alcohol and water liquid fraction may be rectangular as illustrated in FIG. 1, circular as illustrated in FIG. 3, or any shape which would facilitate its function as a drug delivery system for topical anesthetics. The viscoelastic gel pad 10 preferably is approximately 1.0 mm to 5.0 mm thick to be effective as a cushioning and topical anesthetic delivery system.

While the above describes an exemplary preferred embodiment of a topical anesthetic delivery system using lidocaine base, it should be recognized that, more generally, the viscoelastic gel pad may utilize a gel having an alcohol, water, or oleaginous liquid fraction, or a compatible combination thereof, such as the alcohol and water liquid fraction discussed elsewhere herein. A suitable viscoelastic gel pad has been successfully formed by the use of the hydrophilic gel described by King in U.S. Pat. No. 3,419,006, in a pad somewhat larger and conforming to the general shape of the target skin surface which is being anesthetized or otherwise medicated, so as to apply the medication in a prescribed and even manner. The viscoelastic gel pad is simple to utilize, wherein, for example, a hydrophilic gel having been initially hydrated, the water may be evaporated off, and then the desiccated pad soaked in the desired aqueous solution to reconstitute a hydrogel pad with the medication incorporated therein. A polyvinyl alcohol hydrogel may also be used, wherein the medication may be introduced into the gel prior to the gelling reaction. As described in U.S. Pat. No. 5,167,649, a viscoelastic rubber and oil gel pad also may be used, a preferred viscoelastic rubber and oil gel having a rubber component which is a triblock copolymer of styrene-ethylene-butylene-styrene. The rubber component of a viscoelastic rubber and oil gel may be a relatively high molecular weight triblock copolymer of the A-B-A variety where the endblocks are styrene and the rubber midblocks may be saturated olefins, such as ethylene/butylene or ethylene propylene, or unsaturated, such as butadiene or isoprene. In the viscoelastic rubber and oil gel, the oleagenous liquid fraction may be Mineral Oil U.S.P. Other viscoelastic gel formulations having a liquid fraction may also be used, as appropriate.

Many medicinal agents or their salts may be incorporated, such as by dissolution, in the appropriate liquid fraction into the present topical drug delivery system. For example, antifungal agents such as ciclopirox, chloroxylenol, triacetin, sulconazole, nystatin, undecylenic acid, tolnaftate, miconizole, clotrimazole, oxiconazole, griseofulvin, econazole, ketoconozole, and amphotericin B may be incorporated into the liquid fraction of the viscoelastic gel. Antibiotic agents such as mupirocin, erthromycin, clindamycin, gentamicin, polymyxin, bacitracin, silver sulfadiazine, and the like may also incorporated into the present invention. Antiseptic agents such as iodine, Povidine-iodine, benzalkonium chloride, benzoic acid, chlorhexidine, nitrofurazone, benzoyl peroxide, hydrogen peroxide, hexachlorophene, phenol, resorcinol, and cetylpyridinium chloride likewise could be incorporated into the present invention. Furthermore, anti-inflammatories such as hydrocortisone, prednisone, triamcilolone, betamethasone, dexamethasone, and the like may be likewise incorporated. Still further, local anesthetics such as benzocaine, lidocaine to include as described herein, procaine, bupivicaine, an eutectic mixture of prilocaine and lidocaine, phenol, or the like may also incorporated into the liquid fraction of the gel. Additional agents that could be incorporated include penetration enhancers such as dimethyl sulfoxide, ethyl alcohol, isopropyl alcohol, or octolyphenyl-polyethylene glycol, keratolytic agents such as salicylic acid, enzymes such as proteases and nucleases, hormones such as insulin, vesicants such as cantharadin, caustics such as podophyllin, plant and animal venom denaturants such as aluminum sulfate, substance P depleters such as capsiacin, mytotic inhibitors such as anthralin, and a myriad of additional pharmacologically active substances.

Of particular current value is a unique formulation, as described above, whereby lidocaine base, in the form of Lidocaine U.S.P./N.F., may be dissolved in an alcohol and water liquid fraction of a viscoelastic gel, where the alcohol portion of the alcohol and water solution dissolves the lidocaine base (not dissolvable in water) while the water portion provides for absorption and retention in a hydrophilic gel such as described by King in U.S. Pat. No. 3,419,006. Various alcohol and water solutions with between about 20% and 90% alcohol may provide acceptable results, a 70%, by volume, ethyl alcohol solution being preferred, with Lidocaine U.S.P./N.F., dissolved therein in an amount within the range of 10% to 40%, by weight, depending upon the anesthetic strength desired. Such use of Lidocaine U.S.P./N.F. is believed to be novel, previous anesthetic application having utilized lidocaine hydrochloride which is freely soluble in water but apparently too polar to pass through the epidermis, requiring an injection via needle and syringe, or a high pressure jet-injection device.

In use, it may be highly advantageous, such as with the described topical anesthetic device, to instruct the patient to apply the device to a target skin surface location preliminary to arrival at the physician's office or clinic. Thus, rather that having to wait a considerable period for alternative topically applied anesthesia to deaden the target skin surface, the patient is immediately available for surgery or other treatment.

The ability of a patient to apply the present topical medicating device, and particularly as a topical anesthetic device, is enhanced by transparency of the viscoelastic gel pad 10 with liquid fraction, and the partially encapsulating impermeable layers 14, 22. Indeed, tha physician may place a mark upon the target skin surface location providing the patient with an identifiable "target" which is observable through the device.

It is thought that the drug delivery system for the administration of medication, to include topical anesthetics such as lidocaine base, of the present invention and its many attendant advantages will be understood from the foregoing description and that it will be apparent that various changes in form, construction and arrangement of the parts thereof may be made without departing from the spirit and scope of the invention or sacrificing all of its material advantages, the form hereinbefore described being merely an exemplary embodiment thereof.

I claim:

1. A topical anesthetic delivery system, comprising:
   a. a viscoelastic gel pad, having a liquid fraction, a first surface, an opposing second surface and a periphery;
   b. said liquid fraction of said viscoelastic gel pad being formed of both alcohol and water, wherein the percentage of said alcohol, by volume, ranges between twenty percent and ninety percent; said alcohol and water liquid fraction having dissolved therein between ten percent and forty percent, by weight, of lidocaine U.S.P./N.F.;
   c. a first layer of alcohol and water impermeable material covering said first surface of said viscoelastic gel pad; and
   d. a second layer of alcohol and water impermeable material, having an aperture formed therein of less dimension than said second surface of said viscoelastic gel pad; said second layer of alcohol and water impermeable material, except for said aperture, covering said second surface of said viscoelastic gel pad; said aperture being positioned upon said second surface, and within said periphery, of said viscoelastic gel pad;
   e. said first and second layers of alcohol and water impermeable material being joined to form a seal about the periphery of said viscoelastic gel pad, so as to encapsulate said viscoelastic gel pad except for said aperture;
   f. wherein a portion of said second surface of said viscoelastic gel pad is exposed through said aperture and is held in direct contact with an anesthetic target skin surface when applied to a wearer's skin.

2. The topical anesthetic delivery system, as recited in claim 1, wherein said alcohol and water liquid fraction of said viscoelastic gel pad is approximately seventy percent alcohol.

3. The topical anesthetic delivery system, as recited in claim 1, wherein said first and second layers of alcohol and water impermeable material and said viscoelastic gel pad having an alcohol and water liquid fraction are transparent.

4. The topical anesthetic delivery system, as recited in claim 1, wherein, additionally, a means of affixing said second layer of alcohol and water impermeable material to the wearer's skin includes pressure sensitive adhesive.

5. A topical anesthetic delivery system, comprising a viscoelastic gel pad, having a liquid fraction, which incorporates an anesthetic in the form of lidocaine U.S.P./N.F. dissolved in an alcohol and water solution, said alcohol and water solution additionally being said liquid fraction of said viscoelastic gel pad;
   a. said alcohol and water liquid fraction of said viscoelastic gel pad being approximately seventy percent alcohol; and
   b. said alcohol and water liquid fraction of said viscoelastic gel having dissolved therein between ten percent and forty percent, by weight, of lidocaine, U.S.P./N.F.

* * * * *